US012144949B2

(12) United States Patent
Dahiwadkar et al.

(10) Patent No.: US 12,144,949 B2
(45) Date of Patent: Nov. 19, 2024

(54) SYSTEM AND METHOD FOR PREPPING LIQUID

(71) Applicant: 3M INNOVATIVE PROPERTIES COMPANY, St. Paul, MN (US)

(72) Inventors: Avanti Deepak Dahiwadkar, Bangalore (IN); Ramkumar Jeyachandran, Bangalore (IN)

(73) Assignee: Solventum Intellectual Properties, Maplewood, MN (US)

( * ) Notice: Subject to any disclaimer, the term of this patent is extended or adjusted under 35 U.S.C. 154(b) by 515 days.

(21) Appl. No.: 17/433,113

(22) PCT Filed: Feb. 26, 2020

(86) PCT No.: PCT/IB2020/051643
§ 371 (c)(1),
(2) Date: Aug. 23, 2021

(87) PCT Pub. No.: WO2020/174421
PCT Pub. Date: Sep. 3, 2020

(65) Prior Publication Data
US 2022/0040462 A1 Feb. 10, 2022

(30) Foreign Application Priority Data
Feb. 26, 2019 (IN) .............................. 201941007415

(51) Int. Cl.
*A61M 35/00* (2006.01)
*A61B 90/80* (2016.01)

(52) U.S. Cl.
CPC ........... *A61M 35/006* (2013.01); *A61B 90/80* (2016.02); *A61M 2205/3331* (2013.01)

(58) Field of Classification Search
CPC ............................ A61M 35/006; A61B 90/80
See application file for complete search history.

(56) References Cited

U.S. PATENT DOCUMENTS 4,148,318 A * 4/1979 Meyer ................. A61M 35/006
604/3
4,415,288 A * 11/1983 Gordon .................. A47K 7/028
401/133
(Continued)

FOREIGN PATENT DOCUMENTS

CN 101687212 3/2010
EP 0282338 9/1988
(Continued)

OTHER PUBLICATIONS

International Search report for PCT International Application No. PCT/IB2020/051643 mailed on Jun. 9, 2020, 3 pages.

*Primary Examiner* — Susan S Su
*Assistant Examiner* — Ted Yang

(57) ABSTRACT

The system comprises of a fluid container, a replaceable applicator head and a compatible, viscous antiseptic solution. The primary advantage is substantially drip free application. The system is non-vented and non-collapsible. The fluid container is non-compressible and comprises a prepping solution, a threaded spout and a container seal. The applicator head consists of a body to which a foam pad is attached and a channel through which the solution flows into the foam when the applicator head is connected to the fluid container. The applicator head when fixed onto the fluid container breaks the seal and creates a continuous channel that is non-vented for the solution to flow into the foam pad.

13 Claims, 3 Drawing Sheets

(56) References Cited

U.S. PATENT DOCUMENTS

| | | | | |
|---|---|---|---|---|
| 4,498,796 | A * | 2/1985 | Gordon | A47K 7/03 604/3 |
| 4,507,111 | A * | 3/1985 | Gordon | A47L 13/24 604/3 |
| 4,925,327 | A * | 5/1990 | Wirt | B65D 47/42 604/3 |
| 5,240,339 | A * | 8/1993 | DeForest | A45D 34/04 401/266 |
| 5,658,084 | A * | 8/1997 | Wirt | A61M 35/006 401/133 |
| 6,248,085 | B1 * | 6/2001 | Scholz | B65D 47/42 401/152 |
| 6,422,778 | B2 * | 7/2002 | Baumann | B65D 35/56 401/265 |
| 6,488,665 | B1 * | 12/2002 | Severin | A61K 9/0014 604/289 |
| 6,672,784 | B2 * | 1/2004 | Baumann | B65D 47/42 401/203 |
| 6,729,786 | B1 | 5/2004 | Tufts | |
| 7,201,525 | B2 * | 4/2007 | Mohiuddin | A61M 35/003 222/83.5 |
| 7,261,701 | B2 * | 8/2007 | Davis | A61M 35/006 604/289 |
| 7,377,710 | B2 | 5/2008 | Baumann | |
| 7,422,388 | B2 | 9/2008 | Tufts | |
| 7,540,681 | B2 * | 6/2009 | Cybulski | A61M 35/006 401/133 |
| 7,614,811 | B2 * | 11/2009 | Kaufman | A61M 35/006 401/133 |
| 7,866,471 | B2 * | 1/2011 | Callahan | A61M 35/003 206/229 |
| 7,866,907 | B2 * | 1/2011 | Cable, Jr. | A61M 35/003 401/133 |
| 8,083,425 | B2 * | 12/2011 | Kaufman | A61M 35/003 401/133 |
| 8,105,306 | B2 * | 1/2012 | Davis | A61M 35/006 422/28 |
| 8,118,766 | B2 * | 2/2012 | Davis | A61P 17/00 604/289 |
| 8,186,897 | B2 * | 5/2012 | Kaufman | B43M 11/06 401/133 |
| 8,556,529 | B2 * | 10/2013 | Law | A61M 35/006 401/133 |
| 8,801,312 | B2 | 8/2014 | Guzman | |
| 8,858,484 | B2 * | 10/2014 | Casey | B65D 83/0055 604/3 |
| 8,956,065 | B2 * | 2/2015 | Froimson | A61L 2/16 401/263 |
| 8,979,785 | B2 * | 3/2015 | Korogi | A61M 35/006 604/289 |
| 9,016,967 | B2 * | 4/2015 | Law | A61M 35/006 401/206 |
| 9,119,946 | B2 | 9/2015 | Dokken | |
| 9,220,881 | B2 * | 12/2015 | Kaufman | A61L 2/18 |
| 9,283,364 | B2 * | 3/2016 | Lockwood | A61M 35/006 |
| 9,757,551 | B2 | 9/2017 | Degala | |
| 9,821,066 | B2 | 11/2017 | Dokken | |
| 10,448,724 | B1 * | 10/2019 | Wendland | A61M 35/003 |
| 2004/0068218 | A1 * | 4/2004 | Davis | A61M 35/006 401/196 |
| 2004/0267182 | A1 * | 12/2004 | Davis | A61M 35/006 604/2 |
| 2006/0072962 | A1 * | 4/2006 | Cybulski | A61M 35/006 401/196 |
| 2007/0147946 | A1 * | 6/2007 | Cybulski | A61M 35/003 401/133 |
| 2011/0066121 | A1 * | 3/2011 | Hoang | A61M 35/006 29/428 |
| 2012/0219346 | A1 * | 8/2012 | Law | A61M 35/006 401/132 |
| 2016/0332201 | A1 * | 11/2016 | Margoosian | A61M 35/006 |
| 2018/0093082 | A1 * | 4/2018 | Adams | A61M 35/003 |
| 2020/0029848 | A1 * | 1/2020 | Erney | A61B 90/80 |

FOREIGN PATENT DOCUMENTS

| | | | |
|---|---|---|---|
| WO | WO 1999-063934 | 12/1999 | |
| WO | WO-9963934 A2 * | 12/1999 | A01N 59/12 |
| WO | WO-2013067127 A2 * | 5/2013 | A46B 11/0075 |

* cited by examiner

SYSTEM AND METHOD FOR PREPPING LIQUID

CROSS REFERENCE TO RELATED APPLICATIONS

This application is a national stage filing under 35 U.S.C. 371 of PCT/IB2020/051643, filed Feb. 26, 2020, which claims the benefit of Indian application No. 201941007415, filed Feb. 26, 2019, the disclosure of each of which are incorporated herein by reference in their entireties.

FILED OF INVENTION

The disclosure relates to a fluid application device and method having particular utility in the field of medical and related subjects. More particularly, the disclosure relates to articles and methods useful in applying medicines, drugs, or antiseptic solutions.

BACKGROUND SUMMARY

Antiseptic solutions are applied to a patient's body prior to surgery or other invasive medical procedures where there is a risk of catching infection. In developing countries, preparing or "prepping" a patient is done by pouring the antiseptic prepping solution into a sterile bowl, dipping a gauze or sponge in the solution using forceps, tongs or blades and then painting the body with the soaked gauze or sponge. Using this method, there is dripping of solution during prepping and pooling at the sides of the body that can give rise to burns, skin irritation and leads to wastage of solution. This process also requires separate sterile components to aid in application. In developed countries, the sterile bowl gauze and tongs method has been replaced with single use prepping devices like Duraprep.

U.S. Pat. No. 4,925,327 describes a liquid applicator with a porous metering insert to regulate the flow rate of liquid into the foam, this is a single device with no replaceable head.

U.S. Pat. No. 5,658,084 further describes a liquid applicator that has a frangible glass ampoule that holds the solution which is broken to allow liquid to flow into the foam. Glass is a good barrier to ethylene oxide that is used for sterilizing the applicator. Glass prevents exposure of the antiseptic solution to ethylene oxide to maintain the integrity of the liquid. These devices are difficult to manufacture and costly for adoption. Hence, there is a need to create a device that can provide drip free prepping at a lower cost.

U.S. Pat. No. 7,377,710 describes a low cost prepping system, comprising a collapsible container that holds the prepping solution, and a spreader element that can be attached to the container such that the fluid flows from the container into the spreader element that has the foam pad. The collapsible container and its recovery or the collapsible container and the dimensions of the passage of the spreader element serve to control the flow rate or restrict the flow of the prepping solution.

U.S. Pat. No. 6,729,786 describes an applicator with a porous element containing a colorant which will color the liquid before being applied.

U.S. Pat. No. 9,119,946 describes applicator with a first foam with a dye and a second foam lacking the dye to color the applied solution.

EP0282338 describes A disposable container for application of paints, medicaments and coatings having a compressible hollow body with a closed end and a membrane sealed open end, and a stationary applicator housing fitted on said membrane sealed open end so that when said hollow body containing liquid is compressed, said membrane is punctured or fractured and the liquid is supplied to the applicator.

Most applicator designs use a flow control mechanism in the design in the form of a distributor element, a metering device, a valve, or compression. Adding these additional components to the applicator increase its cost and well as manufacturing complexity.

In view of the above disadvantages, there is still a need to develop a simple, cost effective sterile prepping system comprising a prepping device and an integrated, compatible tinting antiseptic solution that is easy to manufacture and use such that the flow of the antiseptic solution can be controlled for uniform spreading and substantially drip free prepping

SUMMARY OF THE INVENTION

The disclosure describes an antiseptic applicator system for surgical prepping to overcome the disadvantages stated above. The system comprises of a fluid container, a replaceable applicator head and a compatible, viscous antiseptic solution. The advantage is a substantially drip free application of solution. The system is non-vented and non-collapsible.

The fluid container is non-compressible and comprises a prepping solution, a threaded spout and a container seal. The applicator head consists of a body to which a foam pad is attached and a channel through which the fluid/solution flows into the foam when the applicator element is connected to the container. The applicator head when fixed onto the fluid container breaks the seal and creates a continuous channel that is non-vented for the solution to flow into the foam pad. The flow is controlled such that there is substantially drip free dispensing and application. Flow control is achieved through a combination of the dimensions of the channel (length to cross sectional area ratio less than 3:1), solution viscosity and foam characteristics. The solution viscosity is altered using a viscosity builder which is preferably a non-ionic, high molecular weight polymer, that is soluble and can build viscosity in water and hydroalcoholic systems. Further, the same viscosity builder can also stabilize the solution in the presence of charged species for example, a solution containing a cationic antiseptic (chlorohexidine) and an anionic tinting agent (anionic dye) by complexing with the anionic agent enabling a longer shelf life of solution and in this case the ability to tint the skin for better visibility. The solution takes preferably less than 30 secs or lower to flow onto the prepping surface once the unit is up turned into a prepping position. The applicator head breaks the seal using a piercing element that prevents the seal from dropping into the solution or blocking the flow of solution into the channel. The system is compatible with ethylene oxide sterilization and has extremely low penetration or evaporation losses. The system is easy to manufacture and use, making it an affordable solution.

BRIEF DESCRIPTION OF THE DRAWINGS

The following drawings illustrate the various embodiments and parts of the claimed devices.

PARTS AND REFERENCE NUMERALS

Figure 1:
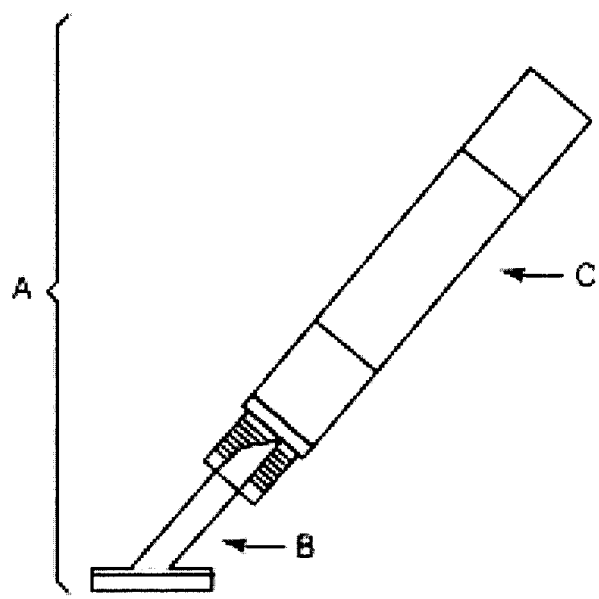
FIG. 1 illustrates system for dispensing a prepping solution.
Figure 2:
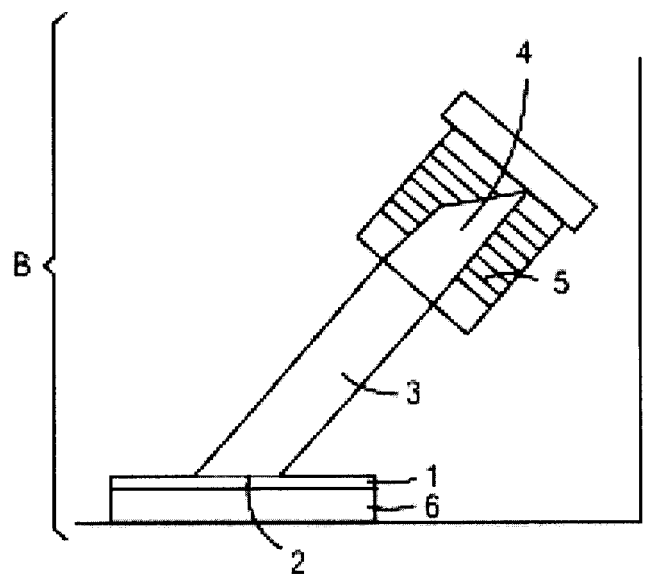
FIG. 2 illustrates the applicator head of the fluid application device.
Figure 3:
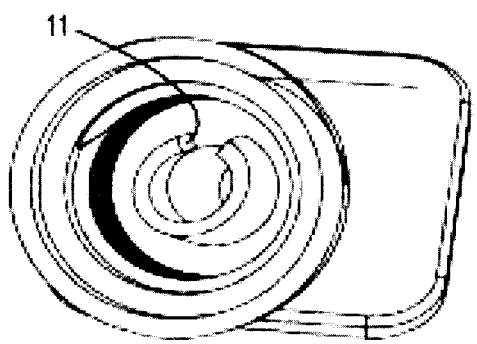
FIG. 3 illustrates the applicator piercer of the fluid application device.
Figure 4:
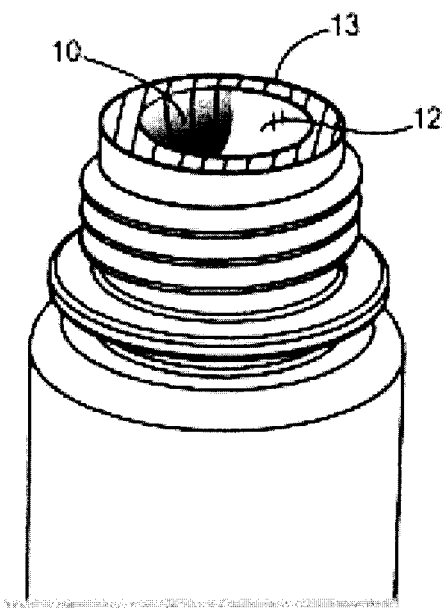
FIG. 4 illustrates the pierced seal of the fluid application device.
Figure 5:
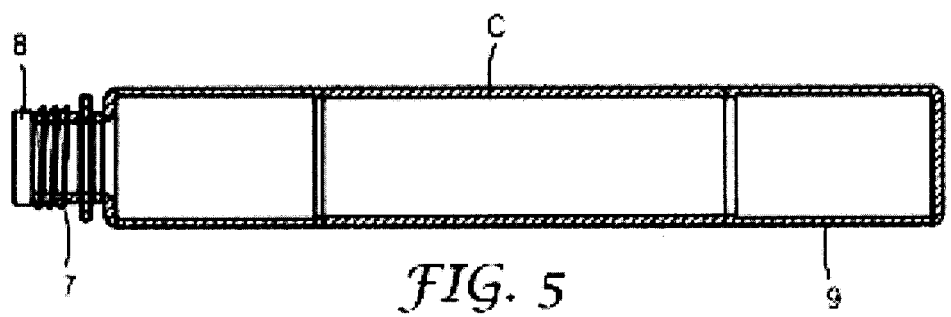
FIG. 5 illustrates container of the fluid application device.

Drip free applicator/Prepping system—(A)
Body—(1)
Orifice—(2)
Channel—(3)
Piercing element/Piercer—(4)
Connecting means/Cap—(5)
Pad—(6)
Connector means/Threaded spout—(7)
Sealing means/Seal—(8)
Fluid container—(C)
Thickness of fluid container—(9)
Pierced seal—(10)
Mini channel—(11)
Opening—(12)
Container lip—(13)

DETAILED DESCRIPTION OF THE INVENTION

Disclosed is a system (A) and method for prepping the fluid from the system. The drip free applicator comprises: a replaceable and attachable applicator head (B) with a pad (6) and piercer (4) to break the seal (8) of the fluid container (C). The fluid container (c) comprises a seal (8) attached to the lid (12) of the fluid container to hold the fluid/prepping solution, (an antiseptic prepping solution in one aspect of the invention), with appropriate viscosity.

The applicator head (B) includes a body (1) with an orifice (2), a channel (3), a piercer (4) and a cap (5) preferably with threads designed to avoid leakage. The channel (3) connects to the fluid container (C), when the seal (8) is broken by the piercer (4) to dispense the fluid.

The channel (3) is connected with an orifice (2) at one end and is connected to the piercer (4) at the other end. The channel (3) acts as the pathway for fluid/prepping solution to flow from fluid container (C) to pad (6). The pad (6) is secured to the bottom side of the orifice (2) and body (1). The channel is secured at an angle of 45 degrees to the pad for ease of prepping. The ratio of length to cross sectional area of said channel (3) is less than 3:1.

The cap (5) embodies internal thread and a provision at the center for the insertion of the channel (3). After the insertion of channel (3) with the piercer (4) in to the cap (5), any gap between the outer circumference of the channel (3) and the provision at the center will be sealed by conventional means to eliminate any leakage of the fluid.

The piercer (4) is designed such that it makes a wide enough opening (12) in the seal (8) by piercing axially. A mini channel (11) in the piercer (4) prevents the blocking of the flow of fluid into the channel (3) due to back pressure or by the broken seal (10). It also prevents floating of the seal (10) in the fluid by leaving a small section of the seal attached to the container lip (13) because of the axial piercing followed by rotational motion to screw the applicator head (B) onto the fluid container (7).

The fluid container (C) contains sufficient quantity of fluid/prepping solution. The fluid container in one embodiment is designed to be rigid and non-collapsible and has a threaded spout (7) for attachment to the applicator head (B) and a seal (8) in the form of an aluminum wad which is broken at the time of attachment by the piercer (4). Once the applicator head (B) is attached to the fluid container (C), the fluid starts flowing from the fluid container (C) to the pad (6) via the channel and the orifice. The thickness (9) and material of the fluid container (C) is chosen to provide a suitable barrier to ethylene oxide penetration into the fluid container (C) and alcohol losses from the fluid container (C). The applicator head (B) after being connected to the fluid container forms a non-vented and non-compressible system.

The surgical prep solution includes skin compatible antimicrobial agents such as iodine or chlorhexidine in sufficient concentration to have the desired effect on the surface. The solution contains a high molecular weight, non-ionic polymer as a viscosity builder to increase the viscosity of the solution for better flow control.

In the case of cationic antiseptic and alcohol solutions, the viscosity builder is chosen from a group of non-ionic, high molecular weight polymers with high polarity that are soluble and can build viscosity in hydro-alcoholic systems (>60% v/v lower alcohols) as well as complex with anionic species for example polyvinylpyrrolidone providing stability and flow control.

The fluid properties of the liquid are tailored using a viscosity builder such that the viscosity and surface tension are compatible with the channel dimensions and foam pad characteristics to control the flow of the prepping liquid into the foam pad and during application on the surface, eliminating the need for additional flow control mechanisms for drip free dispensing and uniform application The applicator head when attached to the container ensures that the device is long enough to prevent the gloves of the clinician coming in contact with the prepping surface and violating aseptic technique. The mode of contact between the container and the applicator head allows the head to be replaced with a new head when required to switch between prepping different parts of the body.

A foam suitable for this application would be a high-density, high porosity felted foam.

The flow regulation is a combination of the following elements such that there is no dripping, at the same time the fluid saturates the foam for prepping within 30 seconds of activation (activation being upturning the device into prepping position)

1) The system is non-collapsible and unvented when the applicator is connected properly to the container, the surgical prep solution moves into the pad under the influence of gravity.
2) Channel dimensions—the length to cross sectional area ratio of the channel being less than 3:1, where the length is measured from the point of fluid entry into the applicator head till the orifice opening into the foam.
3) Viscosity of the fluid between 10 cp to 100 cp.
4) A high-density, high porosity foam with >70 ppi and >40 kg/m3 which has good absorption and retention properties to prevent dripping from the foam even when it is fully soaked.

The seal of the fluid container (C) is reinforced with a cap. The unit is impermeable to ethylene oxide such that it serves as a complete barrier.

The unit is also designed to prevent significant loss of solution over its shelf life.

The exterior surface of the sealed container and the applicator heed can be sterilized using ethylene oxide such that they can be used in an aseptic manner. The scaled container and applicator head(s) are provided in a sterile package.

A. Flow Control

TABLE 1

Impact of channel dimensions, viscosity and foam properties on dripping and time to start prepping

| | Channel dimensions | Viscosity of prep (cp) | Foam Properties | Dripping on application | Time to initiate prepping (secs) | Foam Thickness (mm) |
|---|---|---|---|---|---|---|
| 1 | L = 48 mm<br>Dia = 9.5 mm<br>L/CSA = 0.6 | 35 | ppi >90<br>foam density >=<br>73 kg/m3 | No | 23 | 10 |
| 2 | L = 48 mm<br>Dia = 9.5 mm<br>L/CSA = 0.6 | 52.5 | foam density =<br>114 kg/m3<br>ppi >90 | No | 20 | 10 |
| 3 | L = 48 mm<br>Dia = 9.5 mm<br>L/CSA = 0.6 | 42.5 | foam density =<br>40 kg/m3<br>ppi >= 66 | Yes | 10 | 15 |
| 4 | L = 48 mm<br>Dia = 9.5 mm<br>L/CSA = 0.6 | 0-10 | ppi >90<br>foam density >=<br>73 | Yes | 10 | 10 |
| 5 | L = 48 mm<br>Dia = 9.5 mm<br>L/CSA = 0.6 | 85 | ppi >90<br>foam density >=<br>73 | No | 30 | 10 |

For channel dimensions of 0.6:1, low viscosities below 30 cp drip to an extent, as well as foams with low ppi below 70 and foam density below or equal to 40 kg/m3. At viscosities above 100 cp the solution may take too long to saturate the foam and provide uniform flow as well as take too long to dry.

B. Choice of Viscosity Builder

TABLE 2

Examples of viscosity builders soluble in water or hydro alcoholic systems with >60% v/v of a lower alcohol and can build viscosity >30 cp at a concentration less than 5% w/w. Non-ionic viscosity builders are chosen to eliminate interaction with charged antimicrobial agents.

| Polymer | % w/w | System | Viscosity (cp) | Molecular weight | Antimicrobial agent |
|---|---|---|---|---|---|
| HEC | 1 | Water | 36 | 90,000-1300000 | 10% PVP-I |
| Polyox(WSR N-12K) | 0.6 | Water and hydroalcoholic | 42.72 | 1,000,000 | 2% CHG |
| PVPK 30 | 2.5 | Water and hydroalcoholic | 8 | 40,000-80,000 | 2% CHG |
| PVPK 120 | 2 | Water and hydroalcoholic | 46 | 2,000,000-3,000,000 | 2% CHG |

Figure 6:
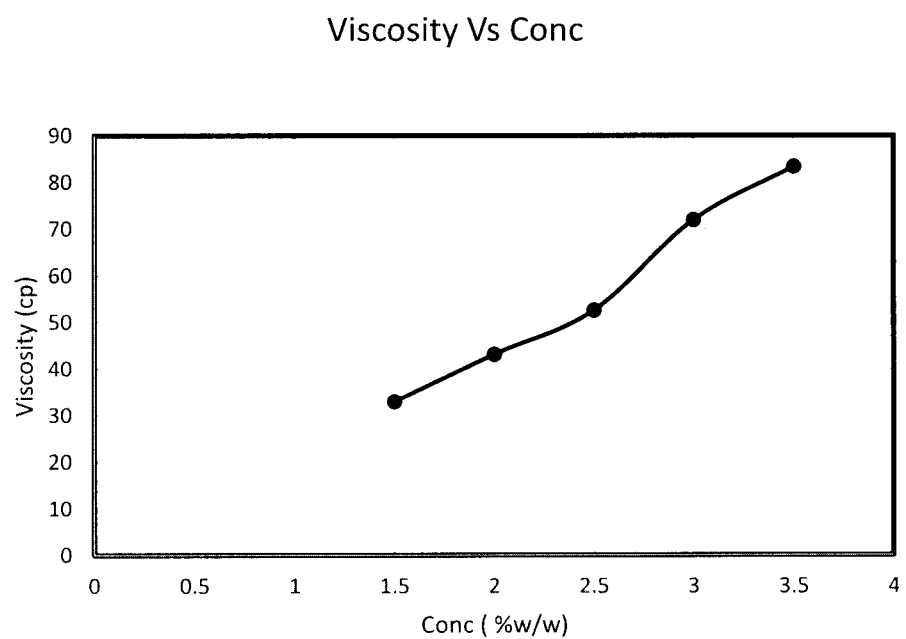
FIG. 6 is a graph showing the relationship between viscosity and concentration.

The graph in FIG. 6 shows that the viscosity gradient increases as the concentration increases. There was substantially less dripping oberved for viscosities above approximately 30 cp corresponding to about 2% PVPK 120 concentration. Prepping was done using a open pore felted PU foam with ppi >70 or foam density >40 kg/m3 and channel dimensions (L/CSA=0.6)

C. Ethylene Oxide Compatibility Studies

The sealed prepping device with 75 ml solution was exposed to ethylene oxide sterilization cycle to evaluate exposure of the solution to EtO and EtO residues.

TABLE 7

Results of ethylene oxide sterilization

| | 1 | 2 |
|---|---|---|
| Liquid Sample (inside device) | | |
| Ethylene Oxide mcg/device | 13 | 13.1 |
| Ethylene Glycol mcg/device | Not detected | Not detected |
| Ethylene Chlorohydrin mcg/device | Not detected | Not detected |

The thickness of the container and seal are designed to serve as an effective barrier to EtO penetration into the container. The ethylene oxide concentration is less than 1 ppm.

D. Alcohol Evaporation or Penetration Losses

Sealed containers with solution were stored at 40 C/75% RH for 5 months.

| Initial weight | Final weight | % wt loss |
|---|---|---|
| 106.57 | 106.46 | 0.10% |
| 106.75 | 106.44 | 0.29% |

The weight loss should be preferably less than 2%.

The fluid container and applicator head (B) are removed from their sterile packaging. The cap that reinforced the fluid container seal (C) is taken off. The applicator head is held in position to axially pierce the seal (0) and pushed down piercing it, followed by threading of the applicator head onto the fluid container. Once, the applicator head (B) is screwed on, the system (A) is upturned allowing the solution to begin flowing into the pad (6). The flow can be activated further by gently compressing the pad (6) against a patient's skin surface.

After the solution reaches the pad (6), prepping of the skin surface can be carried out as per recommended practices based on the antiseptic solution without substantial dripping (eg: zig zag motion for CHG solution, 3 layered prepping for PVP-I with circular motion). The system can be made to stand in between different prepping steps without any dripping from the pad (6). Different areas may be prepped with different applicator heads to prevent contamination from one area to another. To switch to a new applicator head the active applicator head (B) is screwed off and another applicator head can be attached by simply screwing it on and reactivating the flow into the head. Once prepping is completed the solution is allowed to dry.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said fluid is a prepping solution to apply onto a skin surface.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said fluid has a viscosity between 10 cp to 100 cp, preferably 30-60 cp.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said connector means of said tubular container has a sealing means to seal said fluid in said tubular container.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel, wherein said piercing element of said applicator head pierces said seal of said tubular container by rotational or translational motion of said tubular container relative to the applicator head (B).

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said piercing element has a short micro channel opening along its lateral surface area to prevent blockage of flow of fluid into the channel.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said applicator head is removable from the said tubular container and another applicator head can be attached to the said tubular container.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said tubular container is substantially impermeable to ethylene oxide gas.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein external surfaces of said tubular container (C) and the applicator head (B) are sterile.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein said tubular container (C) is non-compressible.

In one embodiment, a drip free applicator for dispensing a fluid comprises: a tubular container with a cavity to store the fluid and a connector means at one end; characterized in that an applicator head with a body, a channel connected to a pad via orifice at one end and a piercing element at other end, and a connecting means disposed around said piercing element; said connector means of said tubular container connected to said connecting means of said applicator head to form a continuous path for said fluid from said tubular container to said pad disposed to receive said fluid from said channel wherein the ratio of length to cross sectional area of said channel (3) is less than 3:1.

The foregoing description is a specific embodiment of the present invention. It should be appreciated that this embodiment is described for purpose of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

What is claimed is:

1. A drip free applicator (A) for dispensing a fluid, the drip free applicator (A) comprising:
    a tubular container (C) comprising:
        a cavity to store the fluid, and
        a connector means (7) at one end; and
    an applicator head (B) comprising:
        a body (1),
        an orifice (2),
        a pad (6),
        a channel (3) connected to the pad (6) via the orifice (2) at one end,
        a piercing element (4) at an end opposite the orifice (2),
        a mini channel (11) along the piercing element (4), wherein the mini channel (11) prevents fluid blockage into the channel (3), and
        a connecting means (5) disposed around the piercing element (4);
    said connector means (7) of said tubular container (C) connected to said connecting means (5) of said applicator head (B) to form a continuous path for the fluid from the tubular container (C) to the pad (6) disposed to receive the fluid from the channel (3).

2. The drip free applicator of claim 1, wherein flow control is a combination of channel dimensions of applicator head (B), viscosity of the fluid, and properties of the pad (6).

3. The drip free applicator of claim 1, wherein the fluid is a prepping solution to apply onto a skin surface.

4. The drip free applicator of claim 3, wherein said fluid has a viscosity between 10 cp to 100 cp.

5. The drip free applicator of claim 1, wherein the connector means (7) of the tubular container (C) comprises a sealing means (8) to seal the fluid in the tubular container (C).

6. The drip free applicator of claim 1, wherein the piercing element (4) of the applicator head (B) pierces the sealing means (8) of the tubular container (C) by rotational or translational motion of the tubular container (C) relative to the applicator head (B).

7. The drip free applicator of claim 1, wherein the pad (6) is a high-density, high porosity foam with >70 ppi and >40 kg/m3, with absorption and retention properties.

8. The drip free applicator of claim 1, wherein the applicator head (B) is removable from the said-tubular container (C) and another applicator head can be attached to the tubular container (C).

9. The drip free applicator in claim 1, wherein said tubular container (C) is substantially impermeable to ethylene oxide gas.

10. The drip free applicator of claim 1, wherein external surfaces of the tubular container (C) and the applicator head (B) are sterile.

11. The drip free applicator of claim 1, wherein the tubular container (C) is non-compressible.

12. The drip free applicator of claim 1, wherein the channel (3) is characterized by a ratio of length to cross sectional area of less than 3:1.

13. A method of dispensing a fluid by an applicator apparatus of claim 1, the method comprising:
    connecting the tubular container (C) with a fluid to the applicator head (B) by piercing a sealing means (8) on the tubular container (C) with the piercing element (4) on the applicator head (B); and
    allowing the fluid to flow into the pad (6), wherein flow is controlled by channel dimensions, pad properties and viscosity of the fluid.

* * * * *